United States Patent [19]

Goldstein

[11] 4,124,700

[45] Nov. 7, 1978

[54] IMMUNOASSAY FOR THYMOPOIETIN

[75] Inventor: Gideon Goldstein, Riverdale, N.Y.

[73] Assignee: Sloan Kettering Institute for Cancer Research, New York, N.Y.

[21] Appl. No.: 810,269

[22] Filed: Jun. 27, 1977

Related U.S. Application Data

[63] Continuation-in-part of Ser. No. 709,565, Jul. 28, 1976, Pat. No. 4,055,633.

[51] Int. Cl.² ...................... G01N 33/16; A61K 43/00
[52] U.S. Cl. ................................. 424/1; 260/112 R; 424/12; 23/230 B
[58] Field of Search ............................. 424/1, 1.5, 12; 23/230 B, 230.6; 260/112 R

[56] References Cited

U.S. PATENT DOCUMENTS 4,055,633  10/1977  Goldstein .................................. 424/1

Primary Examiner—Benjamin R. Padgett
Assistant Examiner—Christine M. Nucker
Attorney, Agent, or Firm—Lowe, King, Price & Becker

[57] ABSTRACT

An immunoassay for the polypeptide thymic hormone thymopoietin is described. Determination of thymopoietin levels in biological fluids provides a useful diagnostic test for myasthenia gravis (elevated levels), immune deficiency diseases (reduced levels), (immunologically mediated diseases such as rheumatoid arthritis, systemic lupus erythematosus and allergy (reduced levels), cancer (reduced levels), malnutrition (reduced levels) and infections (reduced levels). The present assay is also useful as a monitor of the effectiveness of therapy in each of the aforementioned types of disease states.

10 Claims, No Drawings

IMMUNOASSAY FOR THYMOPOIETIN

The invention described herein was made in the course of work under a grant or award from the Department of Health, Education and Welfare.

CROSS-REFERENCE TO RELATED APPLICATION

This is a continuation-in-part application of parent application Ser. No. 709,565, filed July 28, 1976 now U.S. Pat. No. 4,055,633, issued Oct. 25, 1977.

BACKGROUND OF THE INVENTION

Thymopoietin is a polypeptide hormone of the thymus that induces differentiation of prothymocytes to thymocytes and also has secondary effects on neuromuscular transmission. Two forms of bovine thymopoietin, designated thymopoietin I and II have been isolated and shown to be immunologically cross reactive. (Thymopoietin is now used in preference to the original name Thymin). See G. Goldstein, Nature 247, 11 (1974).

Although thymopoietin can be detected by bioassay using either its effects on T cell differentiation or neuromuscular transmission, these assays are complex, time-consuming, and difficult to standardize. Moreover, unlike immunoassay, and particularly radioimmunoassay, bioassays are not readily automated and thus could not be routinely employed by clinical laboratories or other diagnostic facilities to screen large numbers of samples in an economic fashion.

DESCRIPTION OF THE INVENTION

The present invention relates to an immunoassay for thymopoietin. A preferred immunoassay can give sensitivities down to about 0.1 ng/ml. of the hormone in biological fluid samples such as plasma or serum. Thus the instant assay can be employed as a diagnostic test for disease states which exhibit either elevated (myasthenia gravis) or reduced (aging, immune deficiency or immunologically mediated diseases, cancer, malnutrition, infections and the like) levels of thymopoietin. The two forms of thymopoietin are indistinguishable in immunoassay procedures.

The antigen utilized to prepare the antibody for the instant assay is readily obtained by bonding thymopoietin to an immunogenic carrier material in a manner known per se. Such bonding is preferably achieved by employing a suitable bifunctional linking group. A preferred bifunctional linking group for this purpose is a $C_{2-7}$ dialkanal such as glutaraldehyde.

As used herein the term "immunogenic carrier material" is meant to include those materials which have the property of independently eliciting an immunogenic response in a host animal and which can be coupled to thymopoietin. Suitable carrier materials include for example, proteins; natural or synthetic polymeric compounds such as polypeptides, e.g., polylysine or copolymers of amino acids; polysaccharides; and the like. Particularly preferred carrier materials are proteins and polypeptides, especially proteins.

The identity of the protein material utilized in the preparation of an antigen of the instant invention is not critical. Examples of suitable proteins useful in the practice of this invention include mammalian serum proteins such as, for example, human gamma globulin, human serum albumin, bovine serum albumin, methylated bovine serum albumin, rabbit serum albumin, bovine gamma globulin and equine gamma globulin. Other suitable proteins will be suggested to one skilled in the art. It is generally preferred but not necessary that proteins be utilized which are foreign to the animal hosts in which the resulting antigen will be employed.

The coupling of thymopoietin to the immunogenic carrier material can be carried out in a manner well known in the art. Preferred procedures comprise use of covalent bonding or physical bonding, e.g. electrostatically. Thus, for example, when the coupling is carried out to achieve covalent bonding, use of a bifunctional linking group such as glutaraldehyde under the conditions described by S. Avrameas, Immunochemistry 6, 43 (1969) may be employed.

While use of a bifunctional linking group is the preferred manner of achieving covalent bonding of thymopoietin to the immunogenic carrier material, other methods for bonding may also be utilized. In one such method, use may be made of the carbodiimide technique as described in "Science", Vol. 14, pages 1344-1346, June 12, 1964. As reported in this article, carbodiimides can be used to couple materials containing many types of functional groups including carboxylic acids and amines. In this alternate method, coupling proceeds to form covalent bonds by coupling of the thymopoietin to the protein through an amide linkage in the manner described in this article from "Science". A further method of covalent bonding utilizing cyanates which may be used is described in U.S. Pat. No. 3,788,948, issued Jan. 29, 1974.

Bonding of the thymopoietin to the carrier may also be achieved by physical means, for example, by electrostatic bonding, using means known to those skilled in the art. This method proceeds by formation of a complex between the carrier and thymopoietin and may be carried out as described in "Methods in Immunology and Immunochemistry", edited by Curtis A. Williams, Vol. I, Academic Press, (1967). Other methods are described in U.S. Pat. No. 3,853,987, issued Dec. 10, 1974.

It is, of course, to be understood that other methods known to those skilled in the art may be employed to bond the thymopoietin to the carrier.

The antigens of the present invention may be utilized to induce formation of antibodies specific to thymopoietin in host animals by injecting the antigen in such a host, preferably using an adjuvant such as Freund's adjuvant, using known methods. Improved titres can be obtained by repeated injections over a period of time. Suitable host animals for this purpose include mammals such as rabbits, horses, goats, guinea pigs, rats, cows, sheep, etc. The resulting antisera will contain antibodies which will selectively complex with thymopoietin or an antigen prepared therefrom, as described above.

The specific antibodies for thymopoietin prepared in accordance with the present invention are useful as reagents in an immunoassay for thymopoietin. In a preferred embodiment, antiserum diluted in a suitable buffer such as 5% bovine gamma globulin in 0.1 M phosphate - buffered normal saline, pH 7.4 (BGG - buffer) is mixed with a standard or test sample and also a known amount of radiolabeled thymopoietin, both being dissolved in BGG buffer.

Various methods can then be utilized to determine the amount of thymopoietin present in the test sample. In a first technique, after mixing of the above components and allowing the mixture to stand for several hours at room temperature, the antibody - antigen complex was precipitated using cold 30% polyethylene glycol. After centrifugation, the supernatant is aspirated and the radioactivity in the precipitate counted. The thymopoietin content of the sample can then be determined by comparing the radioactivity level observed to a standard curve in a manner known per se. A suitable standard curve can be obtained by mixing known amounts of thymopoietin with fixed amounts of labeled thymopoietin and the thymopoietin specific antibody and determining the degree of binding for each know amount.

Alternate separation systems for removing the antigenantibody complex may be employed. Such alternate systems are in fact preferred over the polyethylene glycol system described above as they yield greater sensitivity for the assay.

One such system involves the use of a double antibody technique. After the incubation of the three component assay reaction mixture as described above, an antibody elicited in another mammalian species against the primary assay antibody is added, the components mixed, then after standing 5 up to 120 minutes at room temperature, the mixture is centrifuged. After aspiration of the supernatant, the precipitate is counted for radioactivity and the thymopoietin level in the sample determined from a standard curve as above.

The other alternative system employs dextran coated charcoal to assist in separation of the antibody-antigen complex. In this technique, dextran coated charcoal is added to the assay reaction system after incubation. A reduced temperature of about 40° C. is utilized. After standing at about 4° C. for about 30 minutes the mixture is centrifuged and the supernatant aspirated. The precipitate is counted for radioactivity, which in this technique represents "unbound" thymopoietin.

In preferred embodiments of the present assay systems the normal saline utilized in the BGG buffer system is replaced with 4M KCl. This substitution reduces non-specific binding in the assay without concomitant loss of sensitivity.

Suitable labeled thymopoietins for use in the immunoassay of the present invention include radioisotopically labeled thymopoietins, particularly those labeled with tritium ($^3H$), carbon 14($^{14}C$), iodine 125 ($^{125}I$), or with iodine 131($^{131}I$). For other immunoassay embodiments in accordance with this invention one may employ thymopoietins labeled with any other unique and detectable label such as for example chromophores, fluorophors, enzymes, red blood cells, latex particles or electron spin resonance groups.

A most preferred radiolabeled thymopoietin is $^{125}I$ thymopoietin. The introduction of the $^{125}I$ label into thymopoietin can be carried out by procedures known in the art such as by using the chloramine-T method, or more preferably by using the Bolton-Hunter reagent ($^{125}I$ iodinated p-hydroxyphenylpropionic acid, N-hydroxysuccinimide ester) as described in Biochem. J. 133, 529 (1973). This preference is based on the fact that direct iodination of the tyrosyl moieties of thymopoietin results in some loss of immunoreactivity. However, since the Bolton-Hunter reagent condenses with free amino groups it does not affect the immunodeterminant tyrosyl regions.

The remaining above-mentioned labeled thymopoietins are prepared by means known to those skilled in the art. For example, enzyme labeled thymopoietins may be prepared as described in U.S. Pat. No. 3,654,090, issued Apr. 4, 1972. Also, U.S. Pat. No. 3,853,987, issued Dec. 10, 1974, describes methods for use of tracer materials such as fluorescent compounds and latex systems for labeling. Accordingly, such methods of labeling are fully described in the prior art. Thus labeled thymopoietins of the present invention include those radioisotopically labeled, as well as thymopoietins labeled with the other materials mentioned.

The immunoassay of this invention was shown to be specific for thymopoietin by testing with various control polypeptides and observing no displacement of the antibodylabeled anitgen complex. In particular no cross-reaction was obtained with ubiquitin, a material which is widespread in tissues, and with histones, which are extracted from bovine thymus. A synthetic tridecapeptide based on residues 29–41 of thymopoietin, which has the biological activities of thymopoietin did not cross react; apparently this region lacks either the residues and/or the tertiary structure required to reconstitute the antigenic sites recognized by the antithymopoietin antibodies in the antiserum.

The present invention is further illustrated by the following examples.

EXAMPLE 1

Antigen and Antibody Preparation

Thymopoietin was isolated as described by Goldstein, Nature 247, 11 (1974). For immunization, it was coupled to an equal weight of equine gamma globulin with glutaradehyde as the coupling reagent according to the procedure of Avrameas, Immunochemistry 6, 43 (1969). The resulting antigen was then employed in preparing thymopoietin antibody.

Three female San Juan rabbits were each immunized with 400 µg of thymopoietin antigen emulsified in Freunds complete adjuvant and injected intradermally in multiple sites. Immunization was repeated four times at bi-weekly intervals and the animals were bled one week after the last injections.

EXAMPLE 2

Radiolabeling of Thymopoietin (a) Chloramine-T Procedure

Thymopoietin was further purified on carboxymethyl-Sephadex (CM-Sephadex) (0.6 × 30 cm column) equilibrated in 0.2 M ammonium acetate, pH 4.5 and developed with a linear gradient to 0.5 M, pH 4.5. Thymopoietin appeared closely behind the void volume and these fractions were lyophilized and desalted on Sephadex G-25. Purity was established by polyacrylamide gel electrophoresis at pH 4.3 and pH 8.9.

Ten micrograms of the highly purified thymopoietin was radiolabeled with 2 mCi carrier free $^{125}I$ by the chloramine method of Hunter and Greenwood, Nature, 194, 495 (1962) and $^{125}I$ thymopoietin was separated from unreacted radionuclides on Sephadex G-25 (0.6 × cm column) in 0.05 M phosphate, pH 7.5. The column was prewashed with 0.25% gelatin in phosphate buffer. The radioactivity of 1 µl sample from each fraction was determined in an automated gamma spectrometer and the fraction corresponding to the void volume was divided into 0.1 ml. aliquots and stored at -20° C. for use within 3 weeks.

(b) BOLTON-HUNTER PROCEDURE

Two millicuries of $^{125}I$ iodinated p-hydroxyphenylpropionic acid N-hydroxysuccinimide ester (Bolton-Hunter reagent ≈1500 Ci/mmole) dissolved in benzene were utilized to iodinate thymopoietin at 4° C. by the procedure described by Bolten and Hunter, Biochem. J. 133, 529 (1973). The Bolton-Hunter reagent was dried in a fume hood by passing a stream of nitrogen over the mouth of the vial and 10 μl of thymopoietin (0.5 mg/ml. in 0.1 M sodium borate, pH 8.5) were added and held at 4° C. for 45 minutes. Half milliliter of 0.2M glycine in 0.1 M sodium borate, pH 8.5 was then added to react with unconjugated reagent. After 15 minutes $^{125}$I thymopoietin was separated from the other labeled products of the conjugation by the method described in (a) above.

Only 5% of thymopoietin radioiodinated by the chloramine-T method were bound in the presence of excess antibody, this binding decreasing at dilutions greater than $10^{-3}$. By contrast 45% of thymopoietin radioiodinated by the Bolten-Hunter method was bound in the presence of excess antibody; this binding also decreased at antibody dilutions greater than $10^{-3}$.

EXAMPLE 3

(a) Radioimmunoassary-Polyethylene Glycol Separation

Incubations were carried out in triplicate in 12 × 75 mm plastic tubes. To 0.5 ml. of antiserum diluted in 5% bovine gamma globulin in 0.01M phosphate-buffered 0.15M NaCl (BGG buffer) was added 0.2 ml. of sample and 0.3 ml. of $^{125}$I-thymopoietin ($\approx$50,000 cpm in BGG buffer). When serum samples are to be assayed they are prepared by molecular sieve chromatography on G-50 Sephadex in 0.1M ammonium bicarbonate, pH 8.0. The fractions behind the excluded volumn (Vo) and ahead of the included volumne (Vi) are pooled and lyophilized and the resulting powder taken up in buffer for thymopoietin. This preparation serves to exclude molecules of molecular weights higher or lower than thymopoietin from the assay.

The assay tubes are agitated on a vortex mixer and left standing for two hours at room temperature. Half milliliter of cold 30% polyethylene glycol was then added to each tube which was agitated on a vortex mixer and centrifuged at 2,000 rpm in a refrigerated centrifuge for 30 minutes. The supernatants were aspirated and the radioactivity in the precipitates was determined in an automated gamma spectrometer. $^{125}$I thymopoietin precipitated (%) was calculated according to the formula $a-c$ $(b-c) \times 100$ where $a$ = cpm precipitated with antibody, $b$ = total cpm added, and $c$ = cpm precipitated nonspecifically with normal rabbit serum or with antibody and excess unlabeled thymopoietin (these were usually approximately 10% of total cpm). For the standard curve of binding inhibition the thymopoietin bound was calculated as a percentage of maximal thymopoietin binding with antibody at $10^{-1}$. An antibody dilution of 1:3000 was used for the standard curve of binding inhibition.

(b) RADIOIMMUNOASSAY - DOUBLE ANTIBODY SEPARATION

The procedure of (a) above was repeated except that 4M KCl BGG buffer was used and after the two hour incubation period a total of 0.1 ml. of goat anti-rabbit antibody and 0.02 ml. of normal rabbit were added, the components mixed on a vortex mixer, the resulting mixture was allowed to stand at room temperature for 5 minutes and then was centrifuged. The supernatant was aspirated and the precipitate was counted for radioactivity as in (a) above.

(C) RADIOIMMUNOASSAY - DEXTRAN COATED CHARCOAL SEPARATION

Dextran coated charcoal is prepared by mixing equal volumes of (i) 5 gm of Norit A charcoal per 100 ml of phosphate buffer containing 2MKCl and bovine gamma globulin and (ii) 0.5 gm of dextran 110 per 100 ml. of phosphate buffer containing 1M KCl and bovine gamma globulin.

A total 0.5 ml. of dextran coated charcoal is added at 4° C. to the assay tube after the two hour incubation as in (b) above and the mixture allowed to stand at 4° C. for 30 minutes. The tubes are centrifuged and the supernatants aspirated. The pellets are counted for radioactivity which represents "unbound" thymopoietin in this assay.

The binding-inhibition standard curve for unlabeled thymopoietin in the assay employing polyethylene glycol separation of the antigen-antibody complex showed sensitivity to thymopoietin concentrations greater than 5 ng/ml. No significant displacement was produced by control polypeptides which included insulin, alpha-bungarotoxin, ubiquitin, histone and a synthetic tridecapeptide fragment of thymopoietin (residues 29–41) at concentrations of 10 to 1,000 ng./ml.

Binding-inhibition curves for unlabeled thymopoietin in the assays employing the double antibody and dextran coated charcoal separation of the antigen-antibody complex both showed sensitivity to thymopoietin concentrations down to 0.1 ng thymopoietin/ml. These latter two procedures are thus especially suitable for measuring thymopoietin levels in serum samples.

What is claimed is:

1. An antigen consisting essentially of thymopoietin bonded to an immunogenic carrier material.

2. An antigen according to claim 1 wherein bonding of said thymopoietin to said carrier material is by covalent bonding.

3. The antigen of claim 1 wherein said immunogenic carrier material is a protein.

4. The antigen of claim 3 wherein said protein is a mammalian gamma globulin.

5. The antigen of claim 3 wherein said protein is bovine serum albumin.

6. An antibody specific to thymopoietin and to an antigen consisting essentially of thymopoietin bonded to an immunogenic carrier material, said thymopoietin specific antibody being prepared by innoculating a host animal with the aforesaid antigen and collecting the serum from said host animal.

7. The antibody of claim 6 wherein said antigen consists of thymopoietin covalently bonded to a protein.

8. The antibody of claim 7 wherein said protein is bovine serum albumin and said covalent bonding is with glutaraldehyde as a bifunctional linking group.

9. Labeled thymopoietin wherein the label is iodine 131.

10. A method for the radioimmunoassay of thymopoietin in a serum sample, which method comprises mixing said sample with a known amount of radiolabeled thymopoietin and an antibody which will selectively complex with said thymopoietin, separating the resulting antibody-antigen complex from the supernatant, measuring the degree of binding of said radiolabeled thymopoietin in said complex and determining the amount of thymopoientin present in said sample by comparing said degree of binding to a standard curve obtained by mixing known amounts of thymopoietin with fixed amounts of labeled thymopoietin and said antibody, and determining the degree of binding for each known amount of thymopoietin.

* * * * *